United States Patent
Liu et al.

(10) Patent No.: US 11,874,275 B2
(45) Date of Patent: Jan. 16, 2024

(54) METHOD FOR FLUORESCENT IMMUNOASSAY (FIA) AND CHEMILUMINESCENT IMMUNOASSAY (CLIA) BASED ON ELECTROKINETIC ACCELERATION

(71) Applicant: FOSHAN MICROWONDERS BIOTECHNOLOGY CO., LTD., Guangdong (CN)

(72) Inventors: Xiaozhu Liu, Guangdong (CN); Hai Xu, Guangdong (CN); Yanmin Li, Guangdong (CN); Jun Li, Guangdong (CN); Yong Hu, Guangdong (CN); Li Tong, Guangdong (CN); Jie Lin, Guangdong (CN); Zhidong Zhang, Guangdong (CN); Lihua Yang, Guangdong (CN); Liang Ma, Guangdong (CN); Zheng Zeng, Guangdong (CN); Linggao Zeng, Guangdong (CN); Li Chen, Guangdong (CN); Shengxi Wu, Guangdong (CN); Shenghui Qin, Guangdong (CN)

(73) Assignee: FOSHAN MICROWONDERS BIOTECHNOLOGY CO., LTD., Foshan (CN)

( * ) Notice: Subject to any disclaimer, the term of this patent is extended or adjusted under 35 U.S.C. 154(b) by 0 days.

(21) Appl. No.: 18/205,581

(22) Filed: Jun. 5, 2023

(65) Prior Publication Data
US 2023/0324380 A1    Oct. 12, 2023

Related U.S. Application Data

(63) Continuation of application No. PCT/CN2022/085472, filed on Apr. 7, 2022.

(30) Foreign Application Priority Data

May 12, 2021   (CN) .......................... 202110517207.6

(51) Int. Cl.
    *G01N 31/00*    (2006.01)
    *G01N 33/53*    (2006.01)
    *G01N 33/557*   (2006.01)
    *G01N 33/543*   (2006.01)

(52) U.S. Cl.
    CPC ....... *G01N 33/557* (2013.01); *G01N 33/5438* (2013.01)

(58) Field of Classification Search
    None
    See application file for complete search history.

(56) References Cited

FOREIGN PATENT DOCUMENTS

| CN | 101216485 A | 7/2008 |
| CN | 104965081 B | 8/2016 |
| CN | 107367533 A | 11/2017 |
| CN | 107807239 A | 3/2018 |
| CN | 109557150 A | 4/2019 |
| CN | 111665238 A | 9/2020 |
| CN | 112433048 A | 3/2021 |

OTHER PUBLICATIONS

Liu et al. Sensors and Actuators A: Physical 171 (2011) 405-413 (Year: 2011).*
Xiaozhu Liu et al., Development of an AC electrokinetics-based immunoassay system for on-site serodiagnosis of infectious diseases, Sensors and Actuators A: Physical, Aug. 22, 2011, pp. 406-413, vol. 171.
Notice of Allowance of counterpart Chinese Patent Application No. 202110517207.6 dated Jul. 30, 2021.
1st Office Action of counterpart Chinese Patent Application No. 202110517207.6 dated Jun. 30, 2021.
2nd Office Action of counterpart Chinese Patent Application No. 202110517207.6 dated Jul. 26, 2021.

* cited by examiner

*Primary Examiner* — Lisa V Cook

(57) ABSTRACT

The present disclosure relates to the technical field of rapid detection of molecules, and specifically relates to a method for rapid fluorescent immunoassay (FIA) and chemiluminescent immunoassay (CLIA) based on electrokinetic acceleration. The method includes the following steps sequentially: S1. sample acceleration: applying an actuating signal to a chip on which a target molecule is dripped to obtain a chip binding to the target molecule, where the chip includes an electrode sheet and coating molecules is immobilized on the electrode sheet; and S2. secondary antibody acceleration: adding a secondary antibody for binding to the target molecule dropwise on the chip binding to the target molecule, and applying an actuating signal to the chip to obtain a chip binding to the secondary antibody. The method can effectively improve a rate of FIA and CLIA, and can speed up a detection process and meet the need for rapid point-of-care testing (POCT).

16 Claims, No Drawings

METHOD FOR FLUORESCENT IMMUNOASSAY (FIA) AND CHEMILUMINESCENT IMMUNOASSAY (CLIA) BASED ON ELECTROKINETIC ACCELERATION

CROSS-REFERENCE TO RELATED APPLICATIONS

The present application is a continuation application of PCT application No. PCT/CN2022/085472 filed on Apr. 7, 2022, which claims the benefit of Chinese Patent Application No. 202110517207.6 filed on May 12, 2021. The contents of all of the aforementioned applications are incorporated by reference herein in their entirety.

TECHNICAL FIELD

The present disclosure relates to the technical field of rapid detection of molecules, and specifically relates to the bioaffinity assays, e.g. fluorescent immunoassay (FIA) or chemiluminescent immunoassay (CLIA), accelerated by AC electrokinetics.

BACKGROUND

Fluorescent immunoassay (FIA) and chemiluminescent immunoassay (CLIA) are very typical in kinds of immunoassays. Immunoassay is a detection method based on the antigen-antibody specific binding reaction. To perform an immunoassay, a prepared antigen or antibody is used as the probe to capture its corresponding antibody or antigen in a sample. Due to the specificity of immunity, immunoassay methods showed excellent selectivity and were widely used in the detection of kinds of bio-molecules such as pathogens. The FIA combines the specificity and sensitivity of an antigen-antibody reaction and the accuracy of a microtracer, like using the fluorescein as the label, then the antigen-antibody complex with fluorescence can be directly observed by a fluorescence microscope. The chemiluminescence detection is a novel immunoassay technology for detecting trace antigens or antibodies that is established by combining luminescence analysis and an immune response. Chemiluminescence refers to the emission of light that is produced by a chemical reaction.

The current FIA and CLIAFIA or CLIA system usually takes 30 min or more to achieve a detection; and the detection of such a system requires a large sample amount (more than 100 μL), and has a detection limit which is not low enough, these shortcomings hinder their application in the detection of trace substances. A reaction between a biological probe and a target (such as an antigen-antibody reaction) relies on a passive ways such as thermal diffusion, and currently, it is not possible to actively control the immune reaction. The current solution is to use the oven to accelerate the reaction, that is, to heat the overall reaction tank. But the effect is limited. There is an urgent need to develop a method that can effectively increase the FIA and CLIA rate to speed up the detection process and meet the need for rapid point-of-care testing (POCT).

SUMMARY

The present disclosure is intended to provide a method for rapid FIA and CLIA based on electrokinetic acceleration, such as to solve the technical problem that current detection methods have a slow detection speed.

To achieve the above objective, the present disclosure adopts the following technical solutions:

A method for FIA and CLIA based on electrokinetic acceleration is provided, including the following steps sequentially:
- S1. sample acceleration, comprising: dripping sample containing target molecules onto a chip and applying the actuating signal to obtain a chip with bound target molecules, where the chip includes electrodes and coating molecules are immobilized on the electrode sheet; and
- S2. secondary antibody acceleration, comprising: adding a secondary antibody for binding to the target molecules onto the chip bound with the target molecules, and applying an actuating signal to the chip to obtain a chip binding with the secondary antibody.

The principle and advantages of this solution are as follows:

In this solution, on the basis of FIA and CLIA, an electrode of a chip is used to generate a specific electric field, and under an action of this electric field, a local temperature of a sample solution can change and the movement of a target molecule and a secondary antibody in the sample solution can be actively controlled to achieve the rapid binding of the target molecule to coating molecules and the rapid binding of the target molecule to a secondary antibody, thereby accelerating the entire fluorescence immunoassay (FIA) process. During the sample acceleration of S1 and the secondary antibody acceleration of S2, after the actuating signal is applied, an electrophoretic effect is generated to accelerate the movement of the target molecule and the secondary antibody towards the electrode sheet, and an electrothermal effect is generated to form a significant temperature gradient inside the chip, thereby causing a local fluid flow. The temperature effect and the dielectrophoresis (DEP) effect together accelerate the binding of the target molecule and the secondary antibody to the coating molecule and the target molecule on the surface of the electrode sheet, respectively. The actuating signal refers to an alternating current (AC) signal that can promote the movement of molecules in the chip, and characteristic parameters of the actuating signal include a frequency and a voltage.

This solution has the following advantages:

(1) High speed: The entire process can be completed within 5 min, which is one-sixth of a detection time of the traditional FIA and CLIA.

(2) High sensitivity: The introduction of active control can overcome the resistance caused by steric hindrance and concentration distribution and can achieve increased antigen-antibody binding, only about 10 μL of a sample is required, and a trace target molecule in a sample can be detected.

Further, during the sample acceleration of S1 and the secondary antibody acceleration of S2, the actuating signal has a voltage of 5 mV to 40 V and a frequency of 500 Hz to 10 MHz. Under an action of the actuating signal, the target molecule and the secondary antibody can be effectively accelerated to achieve the active control of molecular movement, which can effectively improve the FIA and CLIA rate.

Further, during the sample acceleration of S1 and the secondary antibody acceleration of S2, the actuating signal is applied for 5 s to 90 s. The application time of the actuating signal can ensure the full binding of the target molecule to the coating molecule and the full binding of the target molecule to the secondary antibody. If the application time of the actuating signal is too long, a detection effect cannot be further increased; and if the application time of the actuating signal is too short, a binding effect is poor and a trace substance cannot be detected.

Further, during the secondary antibody acceleration of S2, the secondary antibody is a fluorescent secondary antibody or an enzyme-labeled secondary antibody. The fluorescent secondary antibody can achieve rapid fluorescence detection, and the enzyme-labeled secondary antibody can achieve chemiluminescence detection.

Further, after the secondary antibody acceleration of S2, the method further includes S3. detection, comprising: subjecting the chip binding to the secondary antibody to fluorescence detection or chemiluminescence detection. A fluorescence intensity or a chemiluminescence intensity can be detected to achieve the quantitative or qualitative detection of a target molecule.

Further, during the sample acceleration of S1, a preparation process of the chip includes: a chip coating step for immobilizing the coating molecule on the electrode sheet of the chip; the chip coating step includes preparation of coating molecules solution with a boric acid buffer as a solvent; and the boric acid buffer is prepared as follows: adding a 0.0125 M to 0.05 M sodium tetraborate solution to a 0.05 M to 0.2 M boric acid solution until a pH is 5 to 8.

With the above technical solution, during a process of processing a chip into a finished chip, it is necessary to immobilize coating molecules on an aldehyde-modified electrode sheet through covalent bonding. Generally, in order to ensure the smooth progress of the covalent bonding and ensure the activity of the coating molecule, it is necessary to disperse and dissolve the coating molecule in a buffer. The inventors first adopt the most common phosphate buffered saline (PBS), and it has been found that, although the PBS can ensure a coating effect to some extent, an electrode sheet of a final finished chip is prone to corrosion, and a corroded chip needs to be discarded. The inventors investigate the causes of corrosion through a large number of experiments, and it has been finally found that a type of the buffer is a very critical factor. The inventors test a large number of different buffers, and it has been found that the boric acid buffer (BBS) of the present disclosure has the optimal anti-corrosion effect. The inventors further analyze a reason for the above effect of the boric acid buffer of the present disclosure, and it has been found that a solute in the boric acid buffer can form an anti-oxidation protective layer on a surface of the electrode sheet, thereby preventing the occurrence of corrosion. During the processing of the chip, the use of the boric acid buffer of the present disclosure can overcome the technical problem that a metal electrode sheet can be easily corroded, and can extend a shelf life of the chip and improve a quality of the chip. In addition, a buffer prepared with the above concentrations and pH has an excellent anti-corrosion effect, and if any of the concentrations of boric acid and sodium tetraborate and the pH is higher than or lower than the respective range, an ideal anti-corrosion effect cannot be achieved.

Further, relative to an electrode sheet not immobilized with coating molecules, the electrode sheet immobilized with the coating molecule has a capacitance change rate of −50% to 150%, an impedance change rate of −100% to 100%, a phase change rate of −30% to 30%, a resistance component change rate of −40% to 40%, or an inductance component change rate of −200% to 200%, at a specific impedance scanning frequency.

With the above technical solution, in practical application, before and after the coating molecule is immobilized on the electrode sheet of the chip, an impedance meter is used to scan the chip, and a change curve of the capacitance of the chip with an AC frequency is plotted. Two sets of data before and after the coating molecule is immobilized on the electrode sheet of the chip are analyzed to obtain a specific impedance scanning frequency, and a capacitance change rate at this specific impedance scanning frequency is calculated as follows: capacitance change rate=(capacitance value scanned after coating−capacitance value scanned before coating)/capacitance value scanned before coating×100%. The capacitance change rate needs to be controlled at −50% to 150%, and any chip whose detection result is not within the range needs to be discarded. Experimental results show that, during a quality control process, a capacitance change rate in this range can effectively control a quality of the chip and ensure the stability, homogeneity, and high qualification rate of the chip.

The inventors have found in the chip fabrication process that, when the coating molecule is immobilized on the electrode sheet of the chip according to a process of pretreatment, chip activation, chip film-formation, chip crosslinking, chip coating, and blocking and drying, if a specified quality control manner is not introduced, the quality stability of a final finished chip is very unsatisfactory, and thus there will be many unqualified chips. In order to overcome the above problem, the inventors introduce a quality control procedure in the chip fabrication process, which is a characterization manner of the present disclosure. However, the chip fabrication process is relatively long and involves various technical points, and a step in which the quality control is conducted and a type of the quality control are not reported in the prior art. The inventors first try to strictly detect whether a chip is damaged and contaminated in each step and discard damaged and contaminated chips, and although the qualification rate and stability of finished chips are improved, an improvement effect is still not very desirable. It has been found through a large number of studies that a capacitance change rate before and after the coating molecule is immobilized on the electrode sheet is a key to affecting a quality of the chip (at a specific impedance scanning frequency), and if the upper and lower limits of the capacitance change rate can be set to −50% and 150%, respectively, and any chip with a capacitance change rate beyond the range is discarded, the qualification rate and stability of the obtained finished chips will be significantly improved.

In addition to capacitance, parameters such as impedance, phase, resistance component, and inductance component can be selected for determination. The capacitance, impedance, phase, resistance component, and inductance component all are characteristic parameters of the chip, and are also known as electrical signal values. Change rates of the impedance, phase, resistance component, and inductance component at a specific impedance scanning frequency need to be maintained within specified ranges to ensure the qualification rate of the final products.

In summary, in the process of chip coating, a capacitance change rate, an impedance change rate, a phase change rate, a resistance component change rate, or an inductance component change rate at a specific impedance scanning frequency are detected and calculated, and any chip with a change rate beyond the specified range is discarded, which can effectively eliminate unqualified chips and improve a quality of a finished chip.

Further, before the chip coating step, the preparation process of the chip includes a chip activation step, a chip film-formation step, and a chip crosslinking step sequentially; and the chip activation step includes: subjecting the electrode sheet of the chip to plasma cleaning with air as a medium. An active group can be generated on the surface of the electrode sheet by the plasma cleaning, which is convenient for the subsequent formation of a 3-aminopropyltriethoxysilane (APTES) film. In addition, since air is used as a medium, groups such as —OH, —C=O, and —COOH are generated on the surface through an oxidation reaction; and with nitrogen in the air, a —$NH_2$ group is generated on the surface of the chip, which can achieve the optimal activation effect.

Further, the chip film-formation step includes: covering the electrode sheet after the plasma cleaning with a film formed by APTES. The APTES film formed on the surface of the electrode sheet facilitates the subsequent aldehyde modification.

Further, the chip crosslinking step includes: subjecting the film to aldehyde modification. A specified number of aldehyde groups are stably attached to the electrode sheet, which helps the immobilization of the coating molecule to the electrode sheet. A chip prepared according to this solution has high detection stability, accuracy, and sensitivity.

DETAILED DESCRIPTION

Example 1: Chip Processing

In this example, a chip without coating molecules (antibodies or antigens or other affinity molecules) immobilized is processed into a finished chip coated with an antibody.

The chip used in this example refers to the prior patent CN104965081B of the inventors (Mobile Device-based Antibody/Antigen Detection Method), and it is described in this patent (as shown in FIG. 2 of this patent) that: an antibody/antigen detection system is provided, including at least one reaction unit, where the reaction unit includes a reaction chamber with a top opening; a detection plate is provided at a bottom of the reaction chamber, at least one pair of electrode sheets are laid on the detection plate, and a terminal of each of the electrode sheets passes through and is fixed on a body of the reaction chamber; and a corresponding antigen or antibody for a target antibody or antigen is immobilized on the detection plate. In this example, the chip specifically refers to the reaction unit in CN104965081B, and a structure of the detection plate provided with the electrode sheets can refer to the prior paper of the inventors (Development of an AC electrokinetics-based immunoassay system for on-site serodiagnosis of infectious diseases, Xiaozhu Liu, Sensors and Actuators A, 171 (2011) 406-413, FIG. 3. (b)). Generally, the reaction chamber and the detection plate each are made of a silicon material (Si); and the electrode sheets each are made of a metal material (aluminum, gold, or copper, and aluminum is selected in this example), and the electrode sheets are very easy to be gradually corroded during processing or storage after processing, resulting in the failure of the entire chip. In addition, in order to ensure that the chip can bind to and detect a target molecule, it is necessary to coat the electrode sheet with an antibody (or an antigen or another affinity molecule, which are collectively known as coating molecules) to obtain a finished chip, and the method of processing a chip into a finished chip is improved in the present disclosure.

1. Pretreatment:

A surface of a chip without an antibody coated is observed under a metallographic microscope with 10× eye lens to determine whether electrode sheets of the chip undergo breakage and adhesion (the electrode sheets are parallel to each other) and whether the electrode sheets have other adhered impurities, and a chip that does not undergo breakage and adhesion and has no adhered impurities is selected for the subsequent experiment (which is called a first microscopic examination). The adhered impurities are determined as follows: There should be no spots, particles, dirt, or dust particles with a particle size or length of greater than 0.5 μm at an interdigital site of the electrode sheets (namely, a gap between the electrode sheets), and if there are any, a chip is determined to be unqualified.

2. Chip Activation

A surface of a chip is treated with a plasma cleaner in the prior art under the following parameters to obtain an activated chip: plasma cleaning medium: air, vacuum degree: 0.5 mbar (which can be in a range of 0.3 mbar to 0.5 mbar), power: 50 W (which can be in a range of 50 W to 200 W), and chip treatment time: 10 min (which can be in a range of 5 min to 15 min). This step is intended to clean and modify the surface of the chip. With oxygen in the air, groups such as —OH, —C=O, and —COOH are generated on the surface through an oxidation reaction; and with nitrogen in the air, a —$NH_2$ group is generated on the surface of the chip.

3. Chip Film-Formation

The activated chip is completely immersed (except for the terminal of the chip) in a solution of 10% (mass percentage, which can be in a range of 1% to 10%) APTES in ethanol (APTES is dissolved in absolute ethanol with an APTES mass fraction of 10%), and placed at room temperature (18° C. to 25° C.) for 30 min (which can be in a range of 5 min to 60 min). Each chip is rinsed with a squeeze bottle filled with absolute ethanol for 30 s, and then blow-dried with nitrogen to obtain a chip with a film.

A surface of each chip with a film is observed under a metallographic microscope with eye lens and photographed to record a status of the surface of the chip, and if the surface is damaged or contaminated, the chip is discarded (called a second microscopic examination). A determination method is the same as the determination method in the first microscopic examination.

4. Chip Crosslinking

A qualified chip with a film is cured in a 63° C. (which can be in a range of 50° C. to 100° C.) oven for 60 min, and then cooled to room temperature. 10 μL of a 2.5% (mass percentage, which can be in a range of 1% to 10%) glutaraldehyde solution (prepared with pure water) is added dropwise to a reaction chamber of each chip to cover electrode sheets, and then the chip is placed in a humidifier at room temperature (18° C. to 25° C.) for 1 h (which can be in a range of 0.5 h to 2.0 h). The humidifier has a humidity of 40% (which can be in a range 40% to 60%). Each chip is rinsed with a squeeze bottle filled with ultrapure water (UPW) for 10 s, and then blow-dried with nitrogen to obtain a crosslinked chip.

5. Chip Coating

10 μL of a 10 μg/ml commercial *Brucella* omp 16 antigen solution (a specific coating molecule solution, where a solvent for dispersing and dissolving coating molecules is 100 mM BBS, and according to molecules actually to be detected, different antigens can be selected) is added dropwise to the crosslinked chip, and the chip is incubated at 22° C. (which can be in a range of 18° C. to 25° C.) for 20 h (which can be in a range of 2 h to 24 h) to obtain a coated chip. Then a surface of the chip is observed under a metallographic microscope with 10× eye lens and photographed to record a status of the surface of the chip, and if the surface is heavily damaged or contaminated, the chip is discarded (called a third microscopic examination). A determination method is the same as the determination method in the first microscopic examination.

In this step, BBS (boric acid buffer) is prepared as follows: a 0.0125 M to 0.05 M sodium tetraborate solution is added to a 0.05 M to 0.2 M boric acid solution until a pH is 5 to 8. In this example, 100 mM BBS is specifically prepared as follows: a 0.025 M sodium tetraborate solution is added to a 0.1 M boric acid solution until a pH is 7.4.

6. Blocking and Drying

20 μL of 100 mM BBS is added by a 200 μL pipette to each coated chip and then the chip is blow-dried with nitrogen, which is repeated once. A surface of each chip is observed under a metallographic microscope with 10× eye lens and photographed to record a status of the surface of the chip, and if the surface is heavily damaged or contaminated, the chip is discarded (called a fourth microscopic examination). A determination method is the same as the determination method in the first microscopic examination. 10 μL of a 10% bovine serum albumin (BSA) blocking solution (solvent: 100 mM BBS) is added by a 10 μL pipette dropwise to allow blocking at room temperature for 0.5 h. 20 μL of 100 nM BBS is added by a 200 μL pipette to each chip and then the chip is blow-dried with nitrogen, which is repeated once to obtain a finished chip.

A surface of each chip is observed under a metallographic microscope with 10× eye lens and photographed to record a status of the surface of the chip, and if the surface is heavily damaged or contaminated, the chip is discarded (called a fifth microscopic examination). A determination method is the same as the determination method in the first microscopic examination.

Example 2: Chip Processing

In this example, improvement is conducted on the basis of Example 1, and an impedance scanning quality control procedure is introduced in the "5. Chip coating" process to ensure a yield rate of the chip. It is specifically as follows:

Chip Coating

10 μL of a 10 μg/mL commercial *Brucella* omp 16 antigen solution (a specific coating molecule solution, where a solvent for dispersing and dissolving coating molecules is 100 mM BBS, and according to molecules actually to be detected, different antigens can be selected) is added dropwise to a crosslinked chip, and the chip is incubated for 5 min (which can be in a range of 2 min to 10 min).

An impedance meter is connected to a terminal of an electrode sheet for impedance frequency scanning measurement and analysis. With a scanning frequency range of 1 MHz to 100 Hz (sinusoidal AC), an actuating voltage of 5 mV (which can be in a range of 1 mV to 100 mV), a sampling point number of 201, and a measurement time of 3 s, impedance frequency scanning data of each chip are acquired and saved (which is called impedance scanning before coating, where response parameters of an electrode sheet at different scanning frequencies are acquired, including impedance, phase, resistance component, capacitance component, inductance component, or the like, and a change curve of each of the parameters with the frequency before coating is plotted). After the impedance scanning before coating is completed, the chip is placed in a humidifier and coated at 22° C. (an ambient temperature needs to be controlled) for 20 h (which can be in a range of 2 h to 24 h) to obtain a coated chip. After the coating is completed, the chip is taken out from the humidifier and then scanned by an impedance meter with a scanning frequency of 1 MHz to 100 Hz, an actuating voltage of 5 mV (which can be in a range of 1 mV to 100 mV), a sampling point number of 201, and a measurement time of 3 s. Impedance frequency scanning data of each chip are saved (which is called impedance scanning after coating, where response parameters of an electrode sheet at different scanning frequencies are acquired, including impedance, phase, resistance component, capacitance component, inductance component, or the like, and a change curve of each of the parameters with the frequency after coating is plotted).

The impedance scanning results before coating are compared with the impedance scanning results after coating to determine whether a chip is qualified, and a determination method is as follows: at the above impedance scanning frequency, a change rate of a capacitance value scanned after coating relative to a capacitance value scanned before coating is calculated. A specific calculation method is as follows: capacitance change rate=(capacitance value scanned after coating−capacitance value scanned before coating)/capacitance value scanned before coating×100%. The capacitance change rate needs to be controlled at −50.0% to 150.0%, and a chip with a capacitance change rate beyond this range is an unqualified chip and needs to be discarded. A specific impedance scanning frequency is confirmed by a change curve of capacitance with frequency before coating and a change curve of capacitance with frequency after coating, and a specific confirmation method is as follows: a capacitance change rate between the impedance scanning before coating and the impedance scanning after coating at the same frequency is calculated, and a scanning frequency value corresponding to a maximum value of the capacitance change rate (if the value is a negative number, an absolute value is taken) is the specific impedance scanning frequency. In this example, specifically, the capacitance change rate is calculated at a frequency of 50 KHz (namely, the specific impedance scanning frequency), and the capacitance change rate at the specific impedance scanning frequency is controlled in a range of 60.0% to 100.0%, where the capacitance change rate at the specific impedance scanning frequency is also called the maximum capacitance change rate in scanning before and after coating. Since different chip batches and coating probes lead to different specific impedance scanning frequencies, it is necessary to conduct impedance scanning before and after coating to obtain a specific impedance scanning frequency, and a capacitance change rate at this specific impedance scanning frequency needs to be controlled in a specified range (−50.0% to 150.0%) to ensure a qualification rate of finished chips.

In addition to capacitance, parameters such as impedance, phase, resistance component, and inductance component can be selected for determination. The capacitance, impedance, phase, resistance component, and inductance component all are characteristic parameters of the chip, and are also known as electrical signal values. Change rates of the impedance, phase, resistance component, and inductance component at a specific impedance scanning frequency need to be maintained within specified ranges to ensure the qualification rate of the final products, and the ranges are as follows: impedance change rate: −100% to 100%, phase change rate: −30% to 30%, resistance component change rate: −40% to 40%, and inductance component change rate: −200% to 200%. Impedance change rate=(impedance value scanned after coating−impedance value scanned before coating)/impedance value scanned before coating×100%; phase change rate=(phase value scanned after coating−phase value scanned before coating)/phase value scanned before coating×100%; resistance component change rate=(resistance component value scanned after coating−resistance component value scanned before coating)/resistance component value scanned before coating×100%; inductance component change rate=(inductance component value scanned after coating−inductance component value scanned before coating)/inductance component value scanned before coating× 100%. The parameters such as capacitance, impedance, phase, resistance component, and inductance component correspond to different specific impedance scanning frequencies, and when different parameters are used to characterize a chip, a specific impedance scanning frequency is as follows: a capacitance change rate, an impedance change rate, a phase change rate a resistance component change rate, or an inductance component change rate between the impedance scanning before coating and the impedance scanning after coating at the same frequency is calculated, and a scanning frequency corresponding to a maximum value of the capacitance change rate, the impedance change rate, the phase change rate the resistance component change rate, or the inductance component change rate (if the value is a negative number, an absolute value is taken) is a specific impedance scanning frequency of the parameter (namely, a specific impedance scanning frequency of the capacitance, a specific impedance scanning frequency of the impedance, a specific impedance scanning frequency of the phase a specific impedance scanning frequency of the resistance component, or a specific impedance scanning frequency of the inductance component).

Then a surface of the chip is observed under a metallographic microscope with 10× eye lens and photographed to record a status of the surface of the chip, and if the surface is heavily damaged or contaminated, the chip is discarded (called a third microscopic examination). A determination method is the same as the determination method in the first microscopic examination.

Example 3: Fluorescence Detection Based on Electrokinetic Acceleration

When the finished chip of the present disclosure is used for fluorescence detection, operation steps are as follows:

In this example, the chip prepared in Example 1 is used for detection of an actual sample. Specifically, with detection of a Brucellosis sample (a Brucellosis antibody-positive serum standard sample, where a Brucellosis antibody is a target molecule with an antibody titer of 200,000 IU) as an example, a process of fluorescence detection by the finished chip is illustrated:

1. Sample Acceleration

The Brucellosis sample is added by a 10 μL pipette dropwise on the finished chips with μL of the sample on each chip, and an actuating signal is applied to the chip continuously for 30 s (which can be in a range of 5 s to 90 s). The chip accelerated by the sample is rinsed twice with 20 μL of 1×PBS. In this example, the actuating signal is applied to the chip as follows: an impedance meter is used to treat electrode sheets of the chip at a fixed voltage and a fixed frequency. The fixed voltage and fixed frequency can be in a range of 5 mV to 40 V and a range of 500 Hz to 10 MHz, respectively, which can accelerate the molecular movement and promote the binding of an antibody in the Brucellosis sample to an antigen immobilized on the chip. In this example, the fixed voltage of 2 V and the fixed frequency of 5 kHz are specifically selected.

2. Fluorescent Secondary Antibody Acceleration

A quantum dot (QD)-labeled fluorescent secondary antibody (the secondary antibody is dissolved in 1×PBS at 1 μg/mL, and the secondary antibody here specifically refers to a protein molecule generated through an immune response that can specifically bind to a Brucellosis antibody in sample serum; the antigen immobilized on the chip binds to an antibody in the serum, and the antibody binds to the QD-labeled fluorescent secondary antibody; and the QD used in this example is specifically a polystyrene (PS) fluorescent microsphere of a carbon quantum dot (CQD)) is added by a 10 μL pipette dropwise on the finished chips with 10 μL of the fluorescent secondary antibody on each chip, and an actuating signal (with a fixed voltage of 2 V and a fixed frequency of 5 kHz, where the fixed voltage and the fixed frequency can be in a range of 5 mV to 40 V and a range of 500 Hz to 10 MHz, respectively) is applied to the chip continuously for 30 s (which can be in a range of 5 s to 90 s). The chip accelerated by the sample is rinsed twice with 20 μL of 1×PBS.

3. Fluorescence Detection

An instrument is used to automatically read and calculate a fluorescence intensity with an actuating wavelength of 360 nm and an emission wavelength of 610 nm. A positive test result is obtained in this example, and the target antibody in the Brucellosis sample is successfully detected.

Example 4: Chemiluminescence Detection Based on Electrokinetic Acceleration

Specific steps of chemiluminescence detection by the finished chip are as follows:

1. Sample Acceleration

This section is the same as "1. Sample acceleration" in Example 2.

2. Enzyme-Labeled Secondary Antibody Acceleration

A horseradish peroxidase (HRP)-conjugated secondary antibody (which is an enzyme-labeled secondary antibody and is dissolved in 1×PBS at 1 μg/mL) is added by a 10 μL pipette dropwise on the finished chips with 10 μL of the enzyme-labeled secondary antibody on each chip, and an actuating signal (with a fixed voltage of 2 V and a fixed frequency of 5 kHz, where the fixed voltage and the fixed frequency can be in a range of 5 mV to 40 V and a range of 500 Hz to 10 MHz, respectively) is applied to the chip continuously for 30 s (which can be in a range of 5 s to 90 s). The chip accelerated by the sample is rinsed twice with 20 μL of 1×PBS.

3. Chemiluminescence Detection

10 μL of a Bruno substrate is added to the chip accelerated by the enzyme-labeled secondary antibody, and an instrument is used to automatically read and calculate a chemiluminescence intensity. A positive test result is obtained in this example, and the target antibody in the Brucellosis sample is successfully detected.

Test Example 1: Research on Quality Control and Characterization Conditions 100 chips are prepared by the chip preparation method in Example 2, and 20 of the chips are selected for qualification rate detection (No. 1 in Table 1). In order to test an effect of the quality control characterization method, a comparative experiment is set in this test example, and specific settings are as follows: No. 2: on the basis of Example 2, a limited range of the capacitance change rate is adjusted to −50% to 50%, and a chip with a capacitance change rate beyond this range needs to be discarded; No. 3: on the basis of Example 2, a limited range of the capacitance change rate is adjusted to 80% to 150%, and a chip with a capacitance change rate beyond this range needs to be discarded; No. 4: on the basis of Example 2, a limited range of the capacitance change rate is adjusted to −50% to 150%, and a chip with a capacitance change rate beyond this range needs to be discarded; No. 5: on the basis of Example 2, the microscopic examination quality control process is omitted; No. 6: on the basis of Example 2, the impedance detection quality control process is omitted; No. 7: on the basis of Example 2, the microscopic examination quality control process and the impedance detection quality control process are omitted; No. 8 to No. 10: on the basis of Example 2, a limited range of the capacitance change rate is adjusted, and a chip with a capacitance change rate beyond the range shown in the table needs to be discarded; No. 11 and No. 12: on the basis of Example 2, the control of a capacitance change rate is replaced by the control of an impedance change rate during the impedance detection quality control, and a specific impedance change rate range is limited; No. 13 and No. 14: on the basis of Example 2, the control of a capacitance change rate is replaced by the control of a phase change rate during the impedance detection quality control, and a specific phase change rate range is limited; No. 15 and No. 16: on the basis of Example 2, the control of a capacitance change rate is replaced by the control of a resistance component change rate during the impedance detection quality control, and a specific resistance component change rate range is limited; and No. 17 and No. 18: on the basis of Example 2, the control of a capacitance change rate is replaced by the control of an inductance component change rate during the impedance detection quality control, and a specific inductance component change rate range is limited.

The standard samples to be detected are Brucellosis serum enterprise standard references (10 μL per standard reference, including 10 Brucellosis antibody-positive serum references and 10 Brucellosis-negative serum references). 10 chips are used to detect 10 antibody-positive serum references, and 10 chips are used to detect 10 antibody-positive serum references. The 10 Brucellosis antibody-positive serum references each have an antibody titer of 200,000 IU. After the detection, a qualification rate is counted, and a method for detecting a standard reference is as follows:

A standard sample is added to the chip, then AC is applied by an impedance meter to the chip, and a capacitance change of the electrode sheet is detected. At a fixed frequency, a measurement is conducted continuously for 60 s with a fixed voltage. An average capacitance change rate of the 60 s is calculated, which is a detection result. 10 enterprise negative references and 10 enterprise positive references each are tested, and it is determined whether a chip is qualified according to a detection result and a threshold. A detection threshold is set to 20. When a value of a detection result is greater than 20, it is negative; and when a value of a detection result is less than 20, it is positive. Detection results of the 10 positive controls each should be less than 20, and detection results of the 10 negative controls each should be greater than 20. If the above conditions are not met, a chip is determined to be unqualified. A qualification rate is calculated as follows: qualification rate=number of qualified chips/20×100%. Experimental results are shown in Table 1.

TABLE 1

Impact of a quality control manner on a qualification rate

| No. | Quality control manner | Characteristic parameter | Characteristic parameter change rate | Number of qualified chips | Qualification rate |
|---|---|---|---|---|---|
| 1 | Impedance detection quality control + microscopic examination quality control | Capacitance | 60-100% | 20 | 100.0% |
| 2 | Impedance detection quality control + microscopic examination quality control | Capacitance | −50-50% | 20 | 100.0% |
| 3 | Impedance detection quality control + microscopic examination quality control | Capacitance | 80-150% | 19 | 95.0% |
| 4 | Impedance detection quality control + microscopic examination quality control | Capacitance | −50-150% | 18 | 90.0% |
| 5 | Impedance detection quality control | Capacitance | 60-100% | 15 | 75.0% |
| 6 | Microscopic examination quality control | N/A | N/A | 13 | 65.0% |
| 7 | N/A | N/A | N/A | 8 | 40.0% |
| 8 | Impedance detection quality control + microscopic examination quality control | Capacitance | −100-200% | 15 | 75.0% |
| 9 | Impedance detection quality control + microscopic examination quality control | Capacitance | 100-250% | 15 | 75.0% |
| 10 | Impedance detection quality control + microscopic examination quality control | Capacitance | −150-50% | 16 | 80.0% |
| 11 | Impedance detection quality control + microscopic examination quality control | Impedance | −100-100% | 20 | 100.0% |
| 12 | Impedance detection quality control + microscopic examination quality control | Impedance | −150-150% | 16 | 80.0% |
| 13 | Impedance detection quality control + microscopic examination quality control | Phase | −30-30% | 20 | 100.0% |

TABLE 1-continued

Impact of a quality control manner on a qualification rate

| No. | Quality control manner | Characteristic parameter | Characteristic parameter change rate | Number of qualified chips | Qualification rate |
|---|---|---|---|---|---|
| 14 | Impedance detection quality control + microscopic examination quality control | Phase | −50-50% | 17 | 85.0% |
| 15 | Impedance detection quality control + microscopic examination quality control | Resistance component | −40-40% | 20 | 100.0% |
| 16 | Impedance detection quality control + microscopic examination quality control | Resistance component | −60-60% | 17 | 85.0% |
| 17 | Impedance detection quality control + microscopic examination quality control | Inductance component | −200-200% | 20 | 100.0% |
| 18 | Impedance detection quality control + microscopic examination quality control | Inductance component | −300-300% | 17 | 85.0% |

It can be seen from the results in Table 1 that, when the dual quality control manner of impedance detection quality control and microscopic examination quality control is adopted and the capacitance change rate is controlled at −50% to 150%, an ideal qualification rate of finished chips can be achieved. When a single quality control manner or no quality control is adopted (as shown by experimental data of No. 6 and No. 7), the qualification rate of finished chips is finally decreased. In the impedance detection quality control process, whether a capacitance change rate at a specific frequency is maintained within a specified range is very critical for improvement of the qualification rate. If the capacitance change rate is not within the range of −50% to 150% (as shown by experimental data of No. 8 to No. 10), the qualification rate of finished chips is greatly reduced. When the chips are characterized by the impedance change rate, phase change rate, resistance component change rate, and inductance component change rate to select a chip that meets range requirements and discard a chip that does not meet range requirements, an ideal qualification rate can be achieved (as shown by experimental data of No. 11 to No. 18).

Test Example 2: Research on Corrosion Resistance of Finished Chips

In this test example, buffers in the "5. Chip coating" and "6. Blocking and drying" in Example 1 are investigated. Specifically, a test buffer is used instead of the boric acid buffer in the example, and a finished chip is prepared by the method of the example. A freshly prepared finished chip is placed in a dry sealed bag (in each of tests No. 1 to No. 9, 10 finished chips are adopted, which each are independently packaged in a dry sealed bag), and a surface of the chip (mainly electrode sheets) is observed under a metallographic microscope with 10× eye lens every day to determine whether the electrode sheets are corroded or rusted; and if a corrosion or rusting phenomenon occurs, a date on which the phenomenon occurs is recorded, and an anti-rust time is counted. Experimental results are shown in Table 2.

TABLE 2

Test results of anti-rust time (mean ± SD, N = 10)

| No. | Test buffer type | Preparation method of a test buffer | Anti-rust time (d) |
|---|---|---|---|
| 1 | BBS | As shown in Example 1 | 67.00 ± 3.74 |
| 2 | BBS | A 0.0125M sodium tetraborate solution is added to a 0.05M boric acid solution until a pH is 5.0. | 63.60 ± 3.86 |
| 3 | BBS | A 0.05M sodium tetraborate solution is added to a 0.2M boric acid solution until a pH is 8.0. | 63.20 ± 4.42 |
| 4 | BBS | A 0.025M sodium tetraborate solution is added to a 0.1M boric acid solution until a pH is 9. | N/A |
| 5 | BBS | A 0.025M sodium tetraborate solution is added to a 0.1M boric acid solution until a pH is 4. | N/A |
| 6 | BBS | A 0.1M sodium tetraborate solution is added to a 0.3M boric acid solution until a pH is 7.4. | 55.10 ± 2.47* |
| 7 | BBS | A 0.005M sodium tetraborate solution is added to a 0.02M boric acid solution until a pH is 7.4. | 52.60 ± 3.17* |
| 8 | PBS | As shown by the PBS formula (pH 7.4) | N/A |
| 9 | Carbonic acid buffer | A 0.1M sodium carbonate solution is added dropwise to a 0.1M sodium bicarbonate solution until a pH is 9.0. | N/A |
| 10 | Boric acid solution | 0.1M boric acid solution | N/A |
| 11 | Sodium tetraborate solution | 0.025M sodium tetraborate solution | N/A |

1 L PBS formula (pH 7.4): 0.24 g of potassium dihydrogen phosphate (KDP), 1.44 g of disodium phosphate (DSP), 8 g of sodium chloride, and 0.2 g of potassium chloride are mixed, about 800 mL of deionized water is added, a resulting mixture is thoroughly stirred for dissolution, then a pH is adjusted with concentrated hydrochloric acid to 7.4, and finally a resulting solution is diluted to 1 L. * in Table 2 indicates that data of the experimental group are significantly different from the data of No. 1 (T-test, p<0.05). N/A indicates that the electrode sheets of the chip have largely undergone corrosion during chip processing (which is found by microscopic examination), such that the chip is an unqualified chip; and when the buffers of No. 4, No. 5, and No. 8 to No. 11 are adopted, a qualified finished chip cannot be effectively obtained.

It can be seen from the experimental results that the finished chip prepared by the boric acid buffer of the present disclosure can have a long shelf life, but if a concentration of boric acid or sodium tetraborate in the boric acid buffer is too high or too low, the buffer has a too-high or too-low pH, which is not conducive to the formation of an antioxidant film and leads to a poor anti-corrosion effect of a finished chip. If another buffer is used or the boric acid solution is used alone or the sodium tetraborate solution is used alone, the ideal anti-corrosion effect cannot be achieved.

Test Example 3: Research on Corrosion Resistance of Unprocessed Chips

A chip without coating molecules immobilized (namely, the chip originally obtained in the "1. Pretreatment" step of the example) is placed in a test buffer (immersion), and a surface of the chip (mainly electrode sheets) is observed under a metallographic microscope with 10× eye lens every day to determine whether the electrode sheets are corroded or rusted; and if a corrosion or rusting phenomenon occurs, a date on which the phenomenon occurs is recorded, and an anti-rust time is counted (one chip that has not been processed by the method of the present disclosure is used for each experiment). In this test example, an effect of a test buffer on electrode sheets of different materials is also investigated, and experimental results are shown in Table 3.

TABLE 3

Test results of anti-rust time

| No. | Test buffer | Preparation method of a test buffer | Anti-rust time |
|---|---|---|---|
| 1 | BBS | As shown in Example 1 | 3 d |
| 2 | BBS | A 0.0125M sodium tetraborate solution is added to a 0.05M boric acid solution until a pH is 5.0. | 3 d |
| 3 | BBS | A 0.05M sodium tetraborate solution is added to a 0.2M boric acid solution until a pH is 8.0. | 3 d |
| 4 | BBS | A 0.025M sodium tetraborate solution is added to a 0.1M boric acid solution until a pH is 9. | 1 d |
| 5 | BBS | A 0.025M sodium tetraborate solution is added to a 0.1M boric acid solution until a pH is 4. | 1 d |
| 6 | BBS | A 0.1M sodium tetraborate solution is added to a 0.3M boric acid solution until a pH is 7.4. | 1 d |
| 7 | BBS | A 0.005M sodium tetraborate solution is added to a 0.02M boric acid solution until a pH is 7.4. | 1 d |
| 8 | PBS | As shown by the PBS formula (pH 7.4) | 1 d |
| 9 | Carbonic acid buffer | A 0.1M sodium carbonate solution is added dropwise to a 0.1M sodium bicarbonate solution until a pH is 9.0. | 1 d |

It can be seen from the experimental results that the boric acid buffer of the present disclosure provides a prominent anti-corrosion effect for the electrode sheets. When a pH of the buffer is too high or too low, it is not conducive to the formation of an antioxidant film, resulting in a poor anti-corrosion effect of the electrode sheets. If another buffer is used, the ideal anti-corrosion effect cannot be achieved.

Test Example 4: Research on Chip Activation and Chip Film-Formation Conditions

In this test example, the chip activation and chip film-formation conditions are investigated. No. 1: the chip prepared in Example 2 is adopted; No. 2: an APTES concentration is 5%, and other conditions and treatment methods are the same as in Example 2; No. 3: an APTES concentration is 1%, and other conditions and treatment methods are the same as in Example 2; No. 4: nitrogen is used instead of air as the medium in the chip activation step, and other conditions and treatment methods are the same as in Example 2; No. 5: oxygen is used instead of air as the medium in the chip activation step, and other conditions and treatment methods are the same as in Example 2; No. 6: the "3. Chip film-formation" is directly conducted without the "2. Chip activation", and other conditions and treatment methods are the same as in Example 2; and No. 7: after the "2. Chip activation", the "4. Chip crosslinking" is directly conducted without the "3. Chip film-formation", and other conditions and treatment methods are the same as in Example 2. In each group, 10 finished chips are selected for testing.

At a specific impedance scanning frequency of each chip, a capacitance change rate of the chip between scanning after coating and scanning before coating is calculated, and then the mean and standard deviation (SD) of capacitance change rates of chips are calculated; and an intra-batch coefficient of variation (CV) of a chip before and after coating is calculated according to the following formula: CV=(SD/mean X) 100%. The intra-batch CV of a chip before and after coating is shown in Table 4.

TABLE 4

Experimental grouping and results of the research on chip activation and chip film-formation conditions

| | No. | | | | | | |
|---|---|---|---|---|---|---|---|
| | 1 | 2 | 3 | 4 | 5 | 6 | 7 |
| CV (%) | 10.8 | 11.7 | 12.6 | 25.9 | 27.1 | 36.2 | 61.3 |

It can be seen from Table 4 that the intra-batch CVs of chips No. 1 to No. 3 before and after coating are much lower than that of No. 7, and the formation of an APTES film on a chip obviously facilitates the stable immobilization of coating molecules on the chip, such that the coating molecule is not easy to fall off and the immobilized coating molecule amounts on finished chips produced in a same batch tend to be the same, which ensures the stability of qualities of the finished chips produced in the same batch; the intra-batch CVs of chips No. 1 to No. 3 before and after coating are much lower than that of No. 6, and the finished chips prepared without the chip activation step (even if they are produced in a same batch) are quite different from each other in terms of the immobilized coating molecule amount, resulting in unstable qualities of the finished chips produced in the same batch; and the comparison of No. 1 to No. 3 with No. 4 and No. 5 indicates that the selection of the cleaning medium in the chip activation step will affect the subsequent chip processing steps. In the present disclosure, when air is selected as the cleaning medium, the intra-batch CV of a chip before and after coating can be effectively reduced and the stability of qualities of finished chips can be improved.

In summary, in the present disclosure, air is used as a cleaning medium for plasma cleaning, an APTES film is formed on a chip, and a concentration of APTES in the chip film-formation step is limited in a range of 1% to 10%, which reduces the intra-batch CV of a chip before and after coating, and makes the immobilized coating molecule amounts on finished chips produced in a same batch tend to be the same, thereby improving the stability of qualities of the finished chips produced in the same batch.

The above are merely examples of the present disclosure, and common knowledge such as specific technical solutions and/or characteristics known in the solutions are not excessively described herein. It should be noted that those skilled in the art may further make several variations and improvements without departing from the technical solutions of the present disclosure. These variations and improvements should also be deemed as falling within the protection scope of the present disclosure and will not affect the implementation effect of the present disclosure and the practicability of the patent. The scope of protection claimed in the present application shall be subject to the content of the claims, and the specific implementations in the description may be intended to interpret the content of the claims.

The invention claimed is:

1. A method for fluorescent immunoassay (FIA) and chemiluminescent immunoassay (CLIA) based on electrokinetic acceleration, comprising the following steps sequentially:
   S1. sample acceleration, comprising: dripping a target molecule on a chip and applying an actuating signal to obtain a chip binding with the target molecule, wherein the chip comprises an electrode sheet, coating molecules is immobilized on the electrode sheet, and the coating molecule is provided for binding specifically to the target molecule;
   S2. secondary antibody acceleration, comprising: adding a secondary antibody for binding to the target molecule dropwise on the chip binding with the target molecule, and applying an actuating signal to the chip to obtain a chip binding with the secondary antibody; and
   S3. detection, comprising: subjecting the chip binding with the secondary antibody to fluorescence detection or chemiluminescence detection,
   wherein during the sample acceleration of S1, a preparation process of the chip comprises a chip coating step for immobilizing the coating molecule on the electrode sheet of the chip, wherein at a specific impedance scanning frequency, relative to an electrode sheet not immobilized with coating molecules, the electrode sheet immobilized with the coating molecule has a capacitance change rate of −50% to 150%, an impedance change rate of −100% to 100%, a phase change rate of −30% to 30%, a resistance component change rate of −40% to 40%, or an inductance component change rate of −200% to 200%;
   the chip coating step comprises preparation of coating molecules solution with a boric acid buffer as a solvent; the boric acid buffer is prepared as follows: adding a 0.0125 M to 0.05 M sodium tetraborate solution to a 0.05 M to 0.2 M boric acid solution until a pH is 5 to 8; and a material of the electrode sheet is aluminum.

2. The method for FIA and CLIA based on electrokinetic acceleration according to claim 1, wherein during the sample acceleration of S1, the actuating signal has a voltage of 5 mV to 40 V and a frequency of 500 Hz to 10 MHz; and during the secondary antibody acceleration of S2, the actuating signal has a voltage of 5 mV to 40 V and a frequency of 500 Hz to 10 MHz.

3. The method for FIA and CLIA based on electrokinetic acceleration according to claim 2, wherein during the sample acceleration of S1 and the secondary antibody acceleration of S2, the actuating signal is applied for 5 s to 90 s.

4. The method for FIA and CLIA based on electrokinetic acceleration according to claim 3, wherein during the secondary antibody acceleration of S2, the secondary antibody is a fluorescent secondary antibody or an enzyme-labeled secondary antibody.

5. The method for FIA and CLIA based on electrokinetic acceleration according to claim 1, wherein before the chip coating step, the preparation process of the chip comprises a chip activation step, a chip film-formation step, and a chip crosslinking step sequentially; and the chip activation step comprises: subjecting the electrode sheet of the chip to plasma cleaning with air as a medium.

6. The method for FIA and CLIA based on electrokinetic acceleration according to claim 5, wherein the chip film-formation step comprises: covering the electrode sheet after the plasma cleaning with a film formed by 3-aminopropyl-triethoxysilane (APTES).

7. The method for FIA and CLIA based on electrokinetic acceleration according to claim 6, wherein the chip crosslinking step comprises: subjecting the film to aldehyde modification.

8. The method for FIA and CLIA based on electrokinetic acceleration according to claim 2, wherein before the chip coating step, the preparation process of the chip comprises a chip activation step, a chip film-formation step, and a chip crosslinking step sequentially; and the chip activation step comprises: subjecting the electrode sheet of the chip to plasma cleaning with air as a medium.

9. The method for FIA and CLIA based on electrokinetic acceleration according to claim 3, wherein before the chip coating step, the preparation process of the chip comprises a chip activation step, a chip film-formation step, and a chip crosslinking step sequentially; and the chip activation step comprises: subjecting the electrode sheet of the chip to plasma cleaning with air as a medium.

10. The method for FIA and CLIA based on electrokinetic acceleration according to claim 4, wherein before the chip coating step, the preparation process of the chip comprises a chip activation step, a chip film-formation step, and a chip crosslinking step sequentially; and the chip activation step comprises: subjecting the electrode sheet of the chip to plasma cleaning with air as a medium.

11. The method for FIA and CLIA based on electrokinetic acceleration according to claim 8, wherein the chip film-formation step comprises: covering the electrode sheet after the plasma cleaning with a film formed by APTES.

12. The method for FIA and CLIA based on electrokinetic acceleration according to claim 9, wherein the chip film-formation step comprises: covering the electrode sheet after the plasma cleaning with a film formed by APTES.

13. The method for FIA and CLIA based on electrokinetic acceleration according to claim wherein the chip film-formation step comprises: covering the electrode sheet after the plasma cleaning with a film formed by APTES.

14. The method for FIA and CLIA based on electrokinetic acceleration according to claim 11, wherein the chip cross-linking step comprises: subjecting the film to aldehyde modification.

15. The method for FIA and CLIA based on electrokinetic acceleration according to claim 12, wherein the chip cross-linking step comprises: subjecting the film to aldehyde modification.

16. The method for FIA and CLIA based on electrokinetic acceleration according to claim 13, wherein the chip cross-linking step comprises: subjecting the film to aldehyde modification.

\* \* \* \* \*